United States Patent
Strathmann

(10) Patent No.: US 7,557,069 B2
(45) Date of Patent: Jul. 7, 2009

(54) COMBINATORIAL SYNTHESIS ON ARRAYS

(76) Inventor: Michael Paul Strathmann, 1205 8th Ave. W., Seattle, WA (US) 98119

( * ) Notice: Subject to any disclaimer, the term of this patent is extended or adjusted under 35 U.S.C. 154(b) by 67 days.

(21) Appl. No.: 11/418,568

(22) Filed: May 6, 2006

(65) Prior Publication Data

US 2006/0231412 A1 Oct. 19, 2006

Related U.S. Application Data

(62) Division of application No. 10/322,564, filed on Dec. 17, 2002, now abandoned.

(60) Provisional application No. 60/341,648, filed on Dec. 17, 2001.

(51) Int. Cl.
*C40B 50/00* (2006.01)
*C40B 50/14* (2006.01)
*C40B 50/18* (2006.01)
*C07H 21/00* (2006.01)
*C25B 15/00* (2006.01)

(52) U.S. Cl. .............. 506/30; 506/23; 506/32; 536/25.3; 536/25.31; 205/350

(58) Field of Classification Search ............... 536/25.3, 536/25.31; 506/23, 30, 32; 205/103, 107, 205/118, 205, 219, 220, 221, 229, 414, 350
See application file for complete search history.

(56) References Cited

U.S. PATENT DOCUMENTS 5,837,859 A * 11/1998 Teoule et al. ............ 536/25.3
6,093,302 A * 7/2000 Montgomery ............ 205/122
2002/0008038 A1 * 1/2002 Heller et al. ............ 205/261

* cited by examiner

*Primary Examiner*—Edna Wong

(57) ABSTRACT

The present invention provides methods for synthesizing arrays of polymers. A barrier to a reaction is applied to select features of the array thereby limiting the reaction to the remaining features.

11 Claims, No Drawings

COMBINATORIAL SYNTHESIS ON ARRAYS

1. RELATED APPLICATION DATA

This application is a divisional of U.S. patent application Ser. No. 10/322,564, filed Dec. 17, 2002 now abandoned, which claims benefit of U.S. Provisional Patent Application Ser. No. 60/341,648, filed Dec. 17, 2001.

2. FIELD OF THE INVENTION

The present invention is directed to the synthesis and placement of materials at select locations on a substrate. In particular, the present invention is directed to a method for providing separate sequences of chemical monomers at select locations on a substrate.

3. BACKGROUND

A variety of methods are currently available for making arrays of biological macromolecules, such as arrays of nucleic acid molecules or proteins. One method for making ordered arrays of DNA on a porous membrane is a "dot blot" approach. In this method, a vacuum manifold transfers a plurality, e.g., 96, aqueous samples of DNA from 3 millimeter diameter wells to a porous membrane. A common variant of this procedure is a "slot-blot" method in which the wells have highly-elongated oval shapes. The DNA is immobilized on the porous membrane by baking the membrane or exposing it to UV radiation. This is a manual procedure practical for making one array at a time and usually limited to 96 samples per array. "Dot-blot" procedures are therefore inadequate for applications in which many thousand samples must be determined.

An alternate method of creating ordered arrays of nucleic acid sequences is described by Pirrung, et al. (U.S. Pat. No. 5,143,854, 1992), and also by Fodor, et al. (Science 251:767-773, 1991). The method involves synthesizing different nucleic acid sequences at different discrete regions of a support. This method employs elaborate synthetic schemes, and is generally limited to relatively short nucleic acid sample, e.g., less than 20 bases. A related method has been described by Southern, et al. (Genomics 13:1008-1017, 1992).

Montgomery (U.S. Pat. No. 6,093,302, 2000) teaches a method for making arrays of polymers by employing electrochemically generated reagents that are confined by buffering and/or scavenging agents. The method requires substituting standard chemical reactions that can be used for polymer synthesis (e.g. oligonucleotide chemistry) with tailored electrochemical reactions.

There is a need in the art for a method of synthesizing high-density arrays of polymers that makes use of the many standard chemistries already described for synthesizing individual polymers, including enzymatic techniques. The current invention addresses this problem by making use a barrier to a reaction that can be selectively applied to different features in an array. The use of a barrier minimizes the need to tailor well understood chemical reactions to fit a specific requirement for constructing arrays (e.g. the use of photocleavable protecting groups).

4. BRIEF SUMMARY OF THE INVENTION

The present invention provides methods for synthesizing arrays of polymers. A barrier to a reaction is applied to select features of the array thereby limiting the reaction to the remaining features. The locations of the barrier on the array are determined by an electrochemical process (e.g. electrodeposition, electrodissolution, etc.). The array preferably comprises chemically modified electrodes. By repeating the process and changing the parts of the array to which the barrier is applied, it is possible to construct arrays of polymers (e.g. oligonucleotides, peptides, etc.) using standard chemistries.

5. DETAILED DESCRIPTION OF THE INVENTION

The present invention is designed to provide a barrier to a reaction (e.g. chemical, enzymatic, etc.) at selected locations (or features) in an array while permitting the reaction to occur at other locations in the array (an "array refers to a structure that provides a plurality of spatially addressable locations). After the reaction is finished, the barrier may be removed and applied to a different subset of features. Different reactions may be performed sequentially at different and/or overlapping subsets of features in the array (i.e. combinatorial synthesis) thereby producing an array of different compounds (e.g. oligonucleotides, peptides, small molecules, carbohydrates, materials, etc.).

The barrier is patterned electrochemically with an array of addressable electrodes. Each feature in the array is associated with an electrode. The barrier may be applied everywhere on the array (all the features and any intervening space between the features) and then selectively removed from a subset of features. Alternatively, the barrier may be formed directly on a subset of the features.

In many ways, the present invention is analogous to photolithography in which a barrier is patterned on a surface by light. The barrier is a photoresist and the pattern is determined by a photomask. Indeed, photolithography coupled with standard oligonucleotide synthesis chemistry has been used to synthesize oligonucleotide arrays (Brock, P. J. et al., U.S. Pat. No. 5,658,734). In the instant invention, the photomask is replaced with an array of addressable electrodes, light is replaced with electricity, and the photoresist is replaced with materials that can be electrodeposited and/or electrodissolved either directly or by interaction with an electrochemically generated reagent (e.g. acid, base, radical, etc.).

Methods for making arrays of individually addressable electrodes are well known in the art (see for example, Montgomery, D. D., U.S. Pat. No. 6,093,302; Teoule, R. et al., U.S. Pat. No. 5,837,859; Havens, J. R. et al., U.S. Pat. No. 6,306,348). Microlithography techniques have been used to make arrays with 1000 addressable electrodes (Caillat, P. et al., Sens. Actuators B, 61:154-162, 1999). Arrays with greater than 100,000 electrodes can be constructed, and the electrodes can be less than 1 µM in diameter (Montgomery, D. D., U.S. Pat. No. 6,093,302).

Methods for chemically modifying electrodes are also well known (Fujihira, M., Topics in Organic Chemistry, Plenum, 255-294, 1986). The modified electrodes ("functionalized electrodes") provide functional groups on which solid-phase synthesis can occur (e.g. hydroxyl groups for oligonucleotide synthesis, etc.). For example, chlorosilane and alkoxysilane reagents will react with surface hydroxyls on metal oxide electrodes (e.g., $RuO_2$, doped $SnO_2$, doped $TiO_2$, doped $InO_2$, etc.) and partially oxidized metal electrodes (e.g., platinum, etc.) to provide a variety of functional groups tethered to the electrode by a linker moiety (Murray, R. W., Techniques of Chemistry, Vol. 22, John Wiley & Sons, 1-48, 1992). A wide variety of conducting polymers (e.g. polypyrrole, polyaniline, polythiophene, etc.) with pendant functional groups can be electrochemically deposited on electrodes (Chandrasekhar, P., Conducting Polymers: Fundamentals & Applications, Kluwer, 1999). Composite materials, consisting of a conducting component (e.g. metal, conducting polymer, conducting metal oxide, etc.) and a particulate functionalized component (e.g. $SiO_2$, polystyrene beads, $TiO_2$, etc.) may be electrochemically codeposited on electrodes (Ferreira, C. A. et al., J. Appl. Electrochem. 31:49-56, 2001; Gangopadhyay, R. & De, A., Chem. Mater., 12:608-622, 2000; Musiani, M., Electrochim. Acta, 45:3397-3402, 2000; and Hovestad, A. et al., J. Appl. Electrochem., 29:331-338, 1999). A variety of polymers (e.g. acrylate/polyvinyl alcohol, polysaccharides, polyacrylamides, etc.) may be cast over the entire array of electrodes (Bard, A. J. & Faulkner, L. R., Electrochemical Methods, John Wiley & Sons, 580-589, 2001; Montgomery, D. D., U.S. Pat. No. 6,093,302). Clays, zeolites and other porous structures, such as CPG and sol-gel materials may be coated over the array of electrodes to provide functional groups (Montgomery, D. D., U.S. Pat. No. 6,093,302; Bard, A. J. & Faulkner, L. R., Electrochemical Methods, John Wiley & Sons, 580-589, 2001; Bard, A. J. & Mallouk, T., Techniques of Chemistry, John Wiley & Sons, 271-312, 1992; Havens, J. R. et al., U.S. Pat. No. 6,306,348).

An important element of the invention is the ability to cover the functional groups with a barrier that effectively minimizes the participation of the functional groups and/or appended molecules in a solid-phase synthesis reaction. In this way, only those features in the array that are not covered by the barrier will participate. Whether or not the barrier covers a feature is determined by the voltage (or current) applied to the associated electrode. As mentioned above, an analogy can be drawn between the present invention and photolithography. Much effort has gone into the development of many chemically amplified resists as is known by those skilled in the art. In general, a photoresist is spin-cast on a surface and exposed to light. A photo-acid generator (PAG) produces acid that catalytically affects the structure of the photoresist so it becomes either more or less stable to subsequent exposure to a developer. An analogous procedure can be utilized in the present invention. A resist may be spin-cast on an array of functionalized electrodes. Acid may be generated electrochemically (e.g. through oxidation of water) over select electrodes. In the case of a PAG, acid diffusion is limited by exposure of the resist in the solid phase. The diffusion of electrochemically generated acid may be limited by including a buffer in the solvent (Montgomery, D. D., U.S. Pat. No. 6,093,302). Subsequent treatment of the resist after exposure to acid may follow closely the steps utilized in photolithography (e.g. a post-exposure bake and development). The end result can be a highly cross-linked polymer that provides an effective barrier to solid-phase synthesis (e.g. oligonucleotide chemistry, see McGall, G. et al., Proc. Natl. Acad. Sci. USA, 93:13555-60, 1996). The entire process must be repeated (including stripping the developed resist) for each step in the synthesis (e.g. each nucleotide to be added to the growing oligonucleotide). The above procedure is somewhat cumbersome since each step requires spin-casting and in some cases, baking.

Preferably, the barrier can be deposited directly on the array in solution. Then all subsequent steps in the chemical synthesis may be performed in the same reaction vessel. This process is easily automated by simply moving fluids into and out of the reaction chamber (assuming subsequent reactions are performed in solution). Electrodeposition of polymers is a preferred means for creating a barrier over select, functionalized electrodes. The polymers may be electrochemically polymerized from monomers (e.g. pyrrole, thiophene, aniline, 4-vinyl pyridine, 5-nitroindole, etc.) or the barrier may be formed by electrodeposition of polymers in solution, such as for example polyvinyl ferrocene, polyvinyl alcohol/borate, etc. (Murray, R. W., Techniques of Chemistry, Vol. 22, John Wiley & Sons, 1-48, 1992; Bruckenstein, S. & Pater, E., Anal. Chem., 72:1598-1603, 2000; Zhitomirsky, I. & Petric, A., Mater. Sci. Engin. B, 78:125-130, 2000; Jennings, P. et al., J. Chem. Soc., Faraday Trans., 93:3791-3797, 1997). The electropolymerization of monomers is preferred because the resulting barriers are typically free from defects. During polymerization, pinholes in the film (barrier) are efficiently filled due to increased current fluxes and thus concentration of activated monomer at the pinhole (Murray, R. W., Techniques of Chemistry, Vol. 22, John Wiley & Sons, 1-48, 1992).

After the first solid-phase synthesis step, the electrodeposited polymer must be removed and redeposited on a different set of features (functionalized electrodes) in preparation for the next synthesis step. The barrier must remain insoluble (or at least effectively intact) during the synthesis steps, but must be soluble (or at least removable) under a different set of conditions. Of course, many polymers (and other deposits in general) can be removed simply by changing the solvent or by chemical etching.

Considerable effort has been applied to modifying the solubility properties of conducting polymers (e.g. polypyrrole, polyaniline, polythiophene, etc., see Chandrasekhar, P., Conducting Polymers: Fundamentals & Applications, Kluwer, 1999). Many conducting polymers have increased solubility in their reduced state, such as polyaniline, poly(3-alkylthiophenes), poly(alkoxyethylene dioxythiophene, etc. (Chandrasekhar, P., Conducting Polymers: Fundamentals & Applications, Kluwer, 1999; Izou, K. T. & Gregory, R. V., Synth. Met., 69:109-112, 1995; Czardybon, A. & Lapkowski, M., Synth. Met., 119:161-162, 2001; Hosseini, S. H. et al., Iran Polymer J., 9:255-261, 2000). Indeed, the ability to electrochemically modify the solubility and/or attachment of the polymer barrier is a preferred embodiment of the invention. A preferred monomer is 2,5-di-(2-thienyl)-pyrrole (SNS). The monomer is readily oxidized in acetonitrile and 0.1M $LiClO_4$ to form a film that is insoluble in a variety of organic and aqueous solvents. Upon reduction in acetonitrile/$LiClO_4$, the film electrodissolves back to monomers and soluble oligomers (Brillas, E. et al., J. Electroanal. Chem., 392:55-61, 1995; Carrasco, J. et al., J. Electrochem. Soc., 148:E19-E25, 2001).

The oxidation/reduction of thiol/disulfide groups can be exploited for the reversible electrodeposition or cross-linking of polymers on an electrode (see for example, Naoi, K. et al., J. Electrochem. Soc., 142:354-360, 1995; Endo, K. & Bu, H. -B., J. Electroanal. Chem., 506:155-161, 2001; Bernkop-Schnurch, A. et al., Int. J. Pharmaceutics, 226:185-194, 2001). Electrochemically reversible polymers may be formed from monomers comprising a disulfide bond flanked by groups that can be anodically coupled (see for example, Saito, M. et al., Electrochim. Acta, 45:3021-3028, 2000). In many cases, dissolution of the polymers can be performed chemically in addition to or instead of electrochemically (e.g. a reducing agent such as β-mercaptoethanol may be added to the solution over the deposits). Some deposits (polymers, etc.) may also simply lose adhesion to the surface by varying the voltage of the functionalized electrodes (e.g. potential cycling).

Other types of electrodeposited materials may also provide suitable barriers to synthetic reactions. Electroplating of metals is a well developed art. Metals such as copper, aluminum, gold iron, tin, lead, etc. and their alloys may be electrodeposited from ions in solution (Leith, S. D. et al., J. Electrochem. Soc., 146:1431-1435, 1999; Legrand, L. et al., Electrochim.

Acta 40:1711-1716, 1995; Bakos, I., J. Solid State Electrochem., 4:80-86, 2000; Ramos, A. et al., J. Electrochem. Soc., 148:C315-C321, 2001; Donten, M. et al., Electrochim. Acta, 45:3389-3396, 2000; Krumm, R. et al., Electrochim. Acta, 45:3255-3262, 2000). Metals may be removed from the functionalized electrodes by chemical etching or more preferably by electrodissolution (Datta, M. & Harris, D., Electrochim. Acta, 42:3007-3013, 1997). Similarly, metal oxide/hydroxide barriers may be electrodeposited from solution (e.g. $Cu_2O$, $MnO(OH)$, $CoO(OH)$, $NiO(OH)$, $V_2O_5$, $PbO_2$, $TiO_2$, $ZnO$, $ZrO_2$, etc., see Therese, G. H. A. & Kamath, P. V., Chem. Mater., 12:1195-1204) and subsequently removed by chemical and/or electrochemical means (Bakardjieva, S. et al., J. Solid State Electrochem., 4:306-313, 2000; Isaacs, H. S. et al., Electrochem. Meth. Corrosion, 247:19-24, 1997).

Some barriers may be deposited by electrochemically generated reagents (e.g. base) that can diffuse from the electrode and may lead to deposition at nearby electrodes. To minimize this occurrence, buffers and/or scavengers may be used as taught by Montgomery in U.S. Pat. No. 6,093,302.

Clearly, any material can function as a barrier as long as it satisfies two criteria: 1) the deposition and/or removal of the material at the functionalized electrode is affected by a change in voltage (or current) applied to the electrode, and 2) the material effectively prevents or minimizes a solid-phase reaction at the functionalized electrode on which the material is deposited, but the material does not prevent the reaction at other electrodes that lack deposits. The preferred barrier materials described above are affected by electrochemical processes but more generally, barrier materials may be affected by other processes that can occur at the electrodes such as the generation of light (e.g., light emitting diodes) and heat (e.g. resistors, see for example Caillat, P. et al., U.S. Pat. No. 6,255,677).

The maximum allowable porosity or permeability of the barrier is determined by the solid-phase reaction to be blocked. The diffusion (or movement) of a large enzyme can be minimized by a more porous barrier than is required to block the diffusion of a small molecule like pyridine. In some cases, a reaction component (reagent) may be coupled to a bulkier molecule to prevent diffusion through a very porous barrier (e.g. polyvinyl pyridine may be able to replace pyridine in a reaction, see for example, Sanghvi, Y. S., et al., Organic Process Res. Dev., 4:175-181, 2000). Some reactions will have multiple components of which only one need be blocked by the barrier to prevent the reaction from occurring at the functionalized electrode.

The diffusion of a reaction component (e.g. $Fe^{2+}$) through a barrier may be influenced by the redox state of the barrier. For example, the charge and/or porosity of several conducting polymer films can change depending on whether the film is reduced (insulating state) or oxidized (conducting state), see Stockert, D. et al., Synth. Met., 55:1323, 1993; Maysymiuk, K. & Doblhofer, K., Synth. Met., 55:1382, 1993; Maysymiuk, K. & Doblhofer, K., Electrochem. Acta, 39:217, 1994. In this case, the invention may be practiced without actually physically removing the barrier material from the functionalized electrode. To remove or deposit such a barrier, one simply cycles between the reduced and oxidized forms of the barrier material. This barrier could also provide the functional groups on which synthesis occurs, which would make it part of the functionalized electrode. For example, a polymer membrane used to functionalize an electrode may contain both functional groups and a redox reversible cross-linker (e.g. thiol groups) so that the membrane is highly cross-linked and impermeable under one set of conditions (e.g. oxidized) but is porous under another set of conditions (e.g. reduced).

As described above, the preferred array for the solid-phase synthesis reactions comprises an array of functionalized electrodes. The functional groups are directly attached to the electrode (e.g. silane groups) or they are directly attached to a material that is physically contacting, or proximate to, the electrode (e.g. a membrane coating over the electrode array). Southern teaches a method for electrochemically patterning a surface with an array of electrodes that does not physically contact the surface (U.S. Pat. No. 5,667,667). The electrode array lies adjacent to the surface, separated by electrolyte. Electrochemically generated reagents diffuse or migrate to the surface. Southern's method may be used in the instant invention to affect deposition and/or removal of a barrier on the surface adjacent to the array of electrodes. The functional groups for solid-phase synthesis reside on the surface. For example, a base soluble polymer may be spin cast on the surface to act as a barrier. The array of electrodes is used to generate base (e.g. by reducing water) in order to dissolve the membrane at certain locations on the surface. The surface (or more correctly, the exposed surface) is then subjected to a reaction.

The instant invention lends itself to a wide variety of solid-phase reactions. Indeed, an array of different compounds can be synthesized from essentially any solid-phase reactions that can be combined in a combinatorial manner (see for example, Montgomery, D. D., U.S. Pat. No. 6,093,302; Lebl, L. et al., U.S. Pat. No. 6,045,755; Horlbeck, E. G., U.S. Pat. No. 5,880,972 and references therein). The only requirement is that the barrier be compatible with the chemistry, which typically means the barrier does not break down in the solvents—at least during the time frame of the reaction. In contrast to other array-based combinatorial synthesis methods (Montgomery, D. D., U.S. Pat. No. 6,093,302; Fodor, S. P. A. et al. U.S. Pat. No. 5,445,934), the instant method does not require well-established chemistries (e.g. oligonucleotide synthesis) to be altered in order to function in an array format. In addition, because the synthesis reagents are not generated in situ, combinatorial synthesis methods that utilize enzymes are readily adapted to the present invention (for example, carbohydrate synthesis, Takayama, S., Chem Soc. Rev., 26:407-415, 1997; Nicolau, K. C. & Mitchell, H. J., Angew. Chem. Int. Ed., 40:1576, 2001; Koeller, K. M. & Wong, C.-H., Glycobiology, 10: 1157-1169, 2000).

6. EXAMPLES

6.1 Example 1

The following example demonstrates the synthesis of three different dinucleotides (AC, AG, TT) on an array (at positions 1, 2 & 3, respectively).

An array of four electrodes is made by insertion of four platinum wires (diameter 0.6 mm) into a glass cylinder (diameter 5 mm×height 10 mm). One electrode serves as a counter electrode. The array is inserted into a reaction chamber with a reference electrode (see Teoule, R. et al., U.S. Pat. No. 5,837,859 for details). The three working electrodes are functionalized with a polypyrrole film that contains dimethoxytrityl (DMT) protected hydroxyl groups according to the method taught by Teoule (ibid, Example 4). Briefly, pyrrole and aminoethylpyrrole are copolymerized in the presence of 0.1M $LiClO_4$. The incorporated amine functional groups are coupled to an activated nucleoside. Secondary alcohol groups and unreacted amine functions are blocked with acetic/anhydride/N-methylimidazole in pyridine.

To prepare the electrodes for solid-phase oligonucleotide synthesis, the DMT protected hydroxyls must be deblocked. The array is washed with acetonitrile and transferred to Deblock Solution (3% trichloroacetic acid in dichloromethane) for one minute. The array is washed with acetonitrile and transferred to the electrochemical reaction chamber described above.

In preparation for coupling the first phosphoramidite (C), a barrier must be deposited at positions 2 and 3 of the array, since these positions will possess different residues at the 3'-end (note, synthesis occurs in the 3' to 5' direction). The reaction chamber is filled with the Barrier Solution (5 mM 2,5-di-(2-thienyl)-pyrrole (SNS) and 0.1M LiClO$_4$ in acetonitrile). The barrier is electrodeposited by oxidizing the SNS monomer at electrodes 2 and 3 (that is, the electrodes at position 2 and 3) at constant current (0.5 mA cm$^{-2}$) for 100 seconds at room temperature. The array is washed with acetonitrile and exposed to the "C" Coupling Solution (50 mM DMT-protected deoxycytidine phosphoramidite and 0.25M tetrazole in anhydrous acetonitrile) for 2 minutes at room temperature. Under these conditions, almost all of the exposed hydroxyls at position 1 are coupled to C phoshoramidite while the poly(SNS) barrier minimizes reaction to the hydroxyls at positions 2 and 3.

The array is washed with acetonitrile and the barrier at position 2 is removed by reducing the poly(SNS) film in the Reducing Solution (0.1M LiClO$_4$ in acetonitrile) at constant current (-0.2 mA cm$^{-2}$) until the barrier is completely dissolved (indicated by a rapid drop in voltage relative to the reference electrode). The array is washed with acetonitrile and exposed to the "G" Coupling Solution (50 mM DMT-protected deoxyguanosine phosphoramidite and 0.25M tetrazole in anhydrous acetonitrile) for 2 minutes at room temperature. Here, mainly the exposed hydroxyls at position 2 are coupled because hydroxyls at position 1 are already couple to "C" (thereby protected by the DMT group) and hydroxyls at position 3 are still protected by the poly(SNS) barrier.

The array is washed with acetonitrile and the barrier is removed from position 3 as described above. The array is rinsed with acetonitrile and then exposed to "T" Coupling Solution (50 mM DMT-protected deoxythymidine phosphoramidite and 0.25M tetrazole in anhydrous acetonitrile). Here, "T" couples mainly with the exposed hydroxyls at position 3.

The array is washed with acetonitrile. The phosphite linkages formed in the previous steps are oxidized to the more stable phosphotriester linkage by exposing the array to Oxidizing Solution (0.1M Iodine in water/pyridine/THF 2/20/80) for 1 minute at room temperature. The array is washed with acetonitrile and then exposed to Deblock Solution for one minute in order to remove the DMT protecting groups, thereby exposing hydroxyl groups for coupling the second phosphoramidite in the dinucleotide sequence.

The poly(SNS) barrier is deposited at position 3 as described above. The array is washed with acetonitrile and then exposed to "A" Coupling Solution (50 mM DMT-protected deoxyadenosine phosphoramidite and 0.25M tetrazole in anhydrous acetonitrile).

The array is washed with acetonitrile, the barrier is removed from position 3 as above and the array is exposed to "T" Coupling Solution.

Finally, the array is washed with acetonitrile, exposed to Oxidizer Solution, washed again, exposed to Deblock Solution and washed again to yield the final array of dinucleotides.

6.2 Example 2

A dinucleotide array is synthesized as described in Example 1, except whenever the barrier is removed from one position, it is redeposited at the position (or positions) that just underwent coupling. This step is accomplished by replacing the Reducing Solution with the Barrier Solution. Now, in addition to reducing the poly(SNS) barrier at a selected electrode, the SNS monomer is simultaneously oxidized at another electrode to redeposit the poly(SNS) barrier. Following Example 1, just after "C" is deposited at position 1, the array is washed with acetonitrile. The barrier at position 2 is removed by reducing the poly(SNS) film in the Barrier Solution at constant current (-0.2 mA cm$^{-2}$) while the barrier is electrodeposited by oxidizing the SNS monomer at electrode 1 at constant current (0.5 mA cm$^{-2}$). Now, when the array is exposed to the "G" Coupling Solution, only position 2 is exposed. In this way, if any hydroxyls at position 1 did not couple to "C" during the first step (typically coupling efficiencies are 98-99%), then they will not be exposed to "G".

After the first base has been coupled at all three positions in the array, the poly(SNS) barrier is removed from all the electrodes by reduction in Reducing Solution. The array is washed with acetonitrile and exposed to Capping Solution (8.8% w/v N-methyl imidazole in acetic anhydride/lutidine/THF 1/1/16). This step blocks all the unreacted hydroxyls from coupling to phosphoramidite. As above, the array is exposed to Oxidizer Solution, washed, exposed to Deblock Solution and washed again in preparation for coupling the second phosphoramidite at each position.

The process described above is then repeated for the second phosphoramidite coupled at each position to yield the final dinucleotide array.

I claim:

1. A method for synthesis of an array of separately formed polymers, comprising:
   (a) providing an array comprising distinct features wherein a feature comprises one or more functional groups,
   (b) using an electrochemical process to produce a barrier on a subset of the features such that the barrier prevents a reaction wherein the reaction affects coupling between monomers having at least one protected functional group and the functional groups in the features,
   (c) coupling the monomers to the array,
   (d) removing the barrier,
   (e) deprotecting the functional groups on the monomers coupled to the array, and
   (f) repeating steps (b) through (e) until at least two separate polymers are formed on distinct features of the array.

2. The method of claim 1, wherein the reaction in step (b) enables coupling between the monomers and the functional groups in the features.

3. The method of claim 1, wherein the reaction in step (b) prevents coupling between the monomers and the functional groups in the features.

4. The method of claim 1, wherein the steps of the method are sequential and occur in order.

5. The method of claim 1, wherein step (c) occurs after step (d).

6. The method of claim 1, wherein step (d) occurs after step (e).

7. The method of claim 1, wherein the reaction in step (b) couples the monomers to the functional groups.

8. The method of claim 1, wherein the reaction in step (b) deprotects the protected functional group in the monomers.

9. The method of claim 1, wherein step (f) comprises coupling a second monomer to the array and the second monomer has at least one protected functional group.

10. The method of claim 9, wherein the polymers are oligonucleotides, and the monomers are nucleotide analogs.

11. The method of claim 10, wherein the nucleotide analogs are phosphoramidites and the protected functional group comprises dimethoxytrityl.

* * * * *